United States Patent [19]

Krauter

[11] Patent Number: 4,962,751

[45] Date of Patent: Oct. 16, 1990

[54] HYDRAULIC MUSCLE PUMP

[75] Inventor: Allan I. Krauter, Syracuse, N.Y.

[73] Assignee: Welch Allyn, Inc., Skaneateles Falls, N.Y.

[21] Appl. No.: 357,806

[22] Filed: May 30, 1989

[51] Int. Cl.⁵ .............................................. A61B 1/00
[52] U.S. Cl. ..................................................... 128/4
[58] Field of Search ........................ 128/4, 6; 356/241

[56] References Cited

U.S. PATENT DOCUMENTS

| | | | |
|---|---|---|---|
| 2,844,126 | 7/1958 | Gaylord | 128/4 |
| 3,583,393 | 6/1971 | Takahashi | 128/4 |
| 3,610,231 | 10/1971 | Takahashi | 128/6 |
| 3,669,098 | 6/1972 | Takahashi | 128/6 |
| 3,739,770 | 6/1973 | Mori | 128/6 |
| 3,799,151 | 3/1974 | Fukaumi et al. | 128/6 |
| 4,347,837 | 9/1982 | Hosono | 128/6 |
| 4,700,693 | 10/1989 | Lia et al. | 128/4 |
| 4,762,118 | 8/1988 | Lia et al. | 128/4 |
| 4,762,119 | 8/1988 | Allred, III et al. | 128/4 |
| 4,794,912 | 1/1989 | Lia | 128/4 |
| 4,832,473 | 5/1989 | Ueda | 128/6 X |
| 4,890,602 | 1/1990 | Hake | 128/4 |
| 4,893,613 | 1/1990 | Hake | 128/4 |

Primary Examiner—William H. Grieb
Attorney, Agent, or Firm—Wall and Roehrig

[57] ABSTRACT

This invention comprises four hydraulic muscle pumps connected to four hydraulic dynamic muscles in hermetically sealed pairs to transfer tensive forces from a local to a remote location for use in actuating the articulation section of a borescope or endoscope.

7 Claims, 1 Drawing Sheet

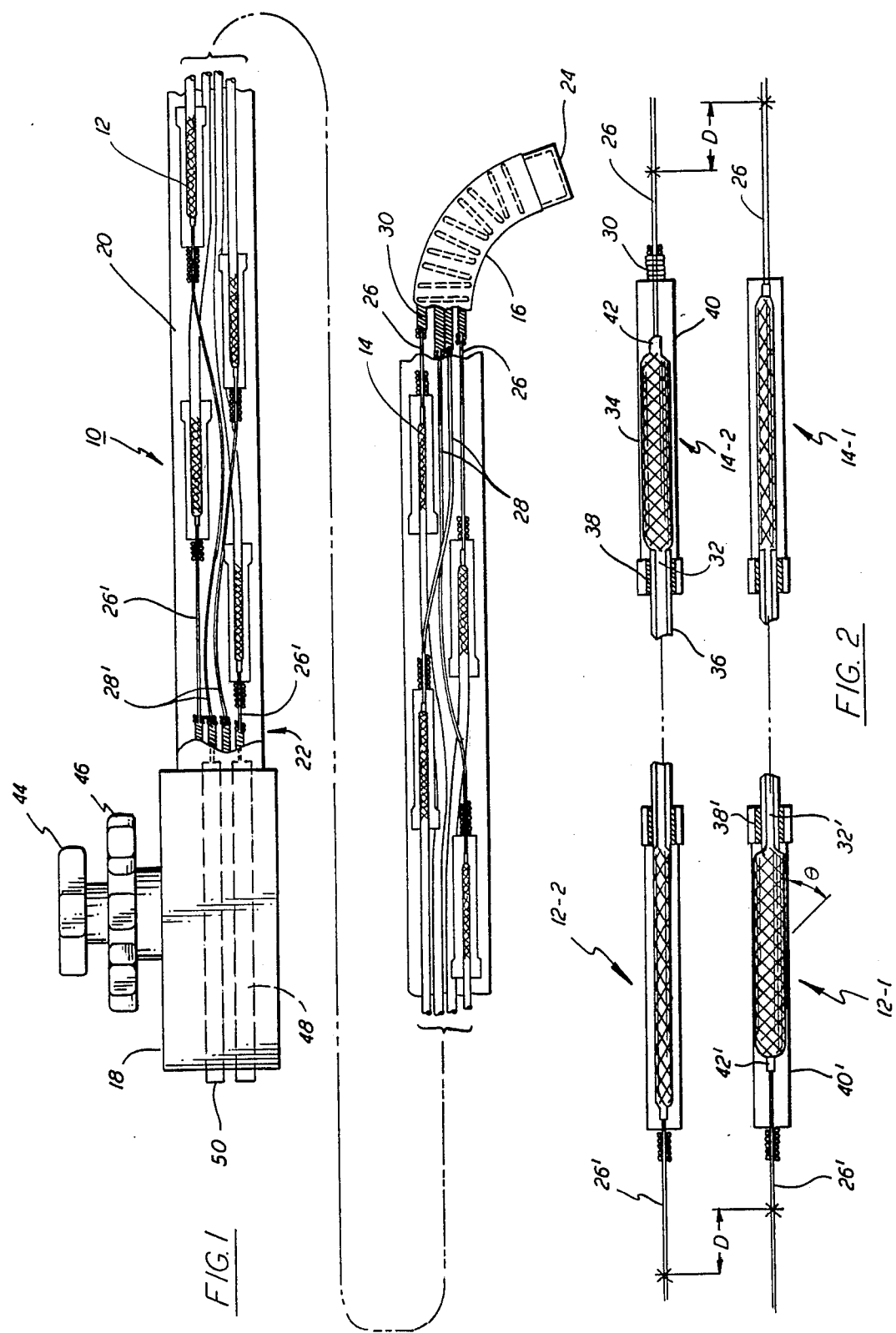

HYDRAULIC MUSCLE PUMP

BACKGROUND OF THE INVENTION

This invention relates to a liquid actuated traction system, and is more particularly concerned with a device which transfers a tensive force via a closed liquid pressure system so as to apply at a remote location a tensive force, to an object to be pulled.

The invention is also directed to a liquid or hydraulic pump which can be incorporated within an elongated insertion tube of a borescope or like device for actuating the articulation or steering section, so that the use of extremely long steering cables can be avoided.

A borescope is generally characterized as an elongated flexible insertion tube with a viewing head at its distal or forward end, and a control housing at its proximal end for controlling or steering the forward end. Such a borescope has a bendable-tube steering section or articulation section at the distal end adjacent the viewing head. One or two pairs of control cables extend through the articulation section, and then through the remainder of the flexible insertion tube. These cables connect with a steering control in the control section. One or both pairs of these cables are differentially displaced to bend the articulation section. The viewing head can thus be remotely oriented to facilitate the inspection of an object. Borescopes are intended for visual inspection of mechanical devices such as jet engines or turbines, where it would be difficult or impossible to examine the device's internal elements directly. The borescope needs to go into narrow tortuous passageways, and must observe similar bending and steering considerations. In addition the pathway to the object can be quite long, and so it is often necessary that the borescope insertion tube be fifteen meters or more in length.

Endoscopes are similar devices, but are intended to be inserted into a body cavity, such as the colon or esophagus, for visual investigation of tissues within the cavity.

A number of types of cable actuated articulation or steering mechanisms are known, and typical ones are discussed in U.S. Pat. Nos. 3,610,231; 3,739,770; 3,583,393; 3,669,098; 3,799,151; and 4,347,837. Another steering mechanism is described in U.S. Pat. No. 4,700,693 having a common assignee herewith.

The articulation mechanisms for those previously-proposed endoscopes and borescopes require that the cables have a significant amount of slack or play because bends and coils in the insertion tube effectively shorten the cables and because the articulation section bends at discrete points rather than follows a smooth curve. However, in both the borescope and endoscope, the articulation section must be bent rather precisely in order to obtain the desired penetration without damaging delicate engine parts or injuring the patient's tissues. For these reasons cable tension must be limited and cable slack must be minimized. Where the insertion tube is long, extra cable slack is often included to accommodate the even greater cable tightening due to the substantial coiling and bending of the insertion tube through which the steering cables pass.

Also, when the cables are differentially displaced to effect articulation, the cable displacement is not precisely reciprocal. That is, the motion of one cable is not the exact opposite of the other. This fact results in undesirable tensioning at some times, and at other times produces unwanted cable slack which can lead to imprecise steering. Coiling of the insertion tube can produce high tension in both cables of a cable pair, which can lead to increased friction and damaging high forces on the cables and on the articulation section. If no measures are taken to compensate for this, early failure can follow. Even when only one cable carries tension, coiling of the insertion tube can produce sufficient friction on the cable to prevent articulation.

PRIOR ART

Ideally, the steering cables should be kept short to avoid the above problems. To do this, the cables would have to terminate within the insertion tube near the articulation section, and some mechanism to draw the cables would be incorporated within the sheath of the insertion tube. Unfortunately, no known existing mechanism had been proposed for this task until U.S. Pat. No. 4,794,912 issued Jan. 3, 1989. (This patent has a common assignee herewith.) This patent shows a method and device for overcoming many of the problems found in these prior borescope/endoscope steering mechanisms. Specifically, in the aforesaid patent there is shown a fluid dynamic muscle mounted adjacent the distal end of the insertion tube which is actuated by pneumatic or hydraulic pressure supplied through small flexible tubes within the borescope insertion tube. The muscle is mounted adjacent the flexible portion of the endoscope/borescope so that the bending cables can be very short and direct in the performance of their bending function without the limitations and problems of the much longer cables referred to in the foregoing prior art.

Thus, as described and claimed in said patent, as fluid pressure is applied to the fluid muscles in the distal end of the borescope, the tube is forced to bend in the desired direction to permit proper viewing, without the problems of extremely long cables that flex, stretch, etc., as described above. This offers a distinct improvement over prior art and allows a much more accurate and precise positioning of the viewing end of the borescope within the cavity being inspected.

As shown in the foregoing patent, the pneumatic muscle system required a source of fluid power at the manipulating end of the borescope. This was indicated in the subject patent as a joystick valve arrangement and a pressure source such as an air compressor.

OBJECTS AND SUMMARY OF THE INVENTION

Since borescopes/endoscopes are frequently used at remote locations and in unusual situations where a readily available source of air or hydraulic pressure is not always possible, it became desirable to provide a self-contained actuating system that took advantage of the fluid muscle previously disclosed without reintroducing the disadvantages of the long, flexible actuating cables of the prior art.

Accordingly, it is an object of the present invention to provide a self-contained liquid actuated system for articulating borescopes, endoscopes, and the like.

It is another object of the present invention to provide a fluid pressure source for a fluid dynamic muscle actuator for the articulation section of a borescope/endoscope.

It is a still further object of the present invention to provide a closed loop hydraulic actuating system for hydraulic muscle actuation of articulation sections of borescopes that does not require any external source of power.

It is yet a further object of the present invention to provide a hydraulic transmission system for transforming mechanical pulling force at a control, to hydraulic activation force, to mechanical pulling force at a remote location.

It is a still further object of the present invention to provide a system for actuation of the articulation section of a borescope/endoscope that minimizes the effective compressibility and elasticity of the actuating systems.

It is a still further object of the present invention to provide a system for actuating the articulation section of a borescope that will operate precisely and accurately over an extended distance from the control apparatus to the distal end of the insertion tube without any external power source.

The above and many other objects, features and advantages of this invention will become apparent from the ensuing description of a preferred embodiment which is to be considered in connection with the accompanying drawings.

BRIEF DESCRIPTION OF THE DRAWING

FIG. 1 is a schematic and partial sectional view showing a borescope that incorporates the hydraulic muscle pump of the present invention with a hydraulic dynamic muscle to actuate the articulation section of the borescope.

FIG. 2 is a partial sectional view on an enlarged scale of a pair of hydraulic muscle pumps and a pair of hydraulic dynamic muscles showing them in cooperative contracted and extended conditions, respectively.

DETAILED DESCRIPTION OF A PREFERRED EMBODIMENT

Referring now to FIG. 1 there is shown a borescope/endoscope 10 embodying four hydraulic muscle pumps 12 according to the present invention with four hydraulic dynamic muscles 14 for actuating the articulation section 16 of a borescope from a control 18. The borescope 10 has an elongated flexible insertion tube 20 with a proximal end 22 and a video imager head 24 disposed at its distal end. Adjacent the head 24 is a steering or articulation section 16. This section is formed of a number of spaced rings or discs and covered with a flexible sheath as is well known in the art. This section has two pair 26 and 28 of steering cables with one pair arranged for bending the articulation section in a first plane and the other pair of cables bending the section in a plane perpendicular to the first plane. Each cable has a flexible sheath 30 which carries the compressive reaction forces corresponding to the tensive force on the associated cable.

Four hydraulic dynamic muscles 14 are arranged in staggered fashion within the distal end of the insertion tube 20 adjacent the articulation section 16 as was shown and described in the above patent. Each hydraulic dynamic muscle 14 has an elongated flexible elastomeric bladder or balloon 32 which is covered with a tubular braid 34 formed of a number of fibers or filaments wound helically around the bladder crossing at a braid angle of $\theta$. A conduit or tube 36 extends from the proximal end of each bladder through the insertion tube 20 to the proximal end 22 thereof. An anchor termination 38 seals the proximal end of both the bladder and braid to the distal end of the conduit 36. A semi-rigid sheath 40 formed typically of a tube of synthetic resin extends distally from the anchor termination 38 and has a closed end through which extends the cable sheath 30 for either steering cable 26 or for either steering cable 28. A forward or distal termination 42 closes the distal end of the braid and connects the same to an associated one of the steering cables 26 or 28.

A corresponding number of hydraulic muscle pumps 12 are positioned at the proximal end of the insertion tube 20 adjacent the controller 18 for the borescope/endoscope. Each of these hydraulic muscle pumps is connected by a conduit 36 to a corresponding hydraulic dynamic muscle 14 at the distal end of the insertion tube. Each hydraulic muscle pump consists of an elongated bladder or balloon 32' anchored at its distal end to a semi-rigid sheath 40' at 38' almost in mirror image to the hydraulic dynamic muscles at the distal end of the insertion tube. The proximal end of each hydraulic muscle pump bladder is terminated and sealed at 42' about a cable 26' or 28' extending to the controller 18 which typically has a pair of control knobs 44 and 46.

The system is connected as shown, and each individual hydraulic pump 12, conduit supply line 36, and hydraulic dynamic muscle 14 is filled with a hydraulic fluid and hermetically sealed as a unit.

The terms "liquid" and "hydraulic fluid" are used herein to denote any liquid that is essentially non-compressible at its working pressure. I have found "Dow Corning 200 Fluid" brand of A Dimethylpolysiloxane to be satisfactory. Generally, the lower the viscosity of the liquid, the better the operation of my device. Also, it is important for some applications that the liquid be non-toxic and as inert as possible.

Before sealing as a unit, one of the hydraulic dynamic muscle bladders 32 is stretched to full length while the corresponding hydraulic muscle pump bladder 32' is expanded to its full diameter for filling. In operation, the bladder at one end of a tube 36 will be in nearly opposite condition to the bladder at the other end, depending on the actuation of the pair of muscles and pumps for each direction of motion of the articulation section of the borescope insertion tube.

Thus, as shown in FIG. 2, the hydraulic muscle pump 12-2 is in the maximum elongated condition and its corresponding hydraulic dynamic muscle 14-2 is in the full expanded position. This pair provides one direction of motion for the articulated section and its companion pair 12-1 and 14-1 can be seen to be in the opposite condition, ready for restoration of the bend of the articulation section 16 to neutral or reverse direction.

The hydraulic muscle pumps 12 are connected by cable pairs 26' and 28' to racks 48 and 50 at the control 18 such that, when it is desired to move the articulated section in one direction, knob 44 is rotated to move rack 48. The upper cable 26' is thereby pulled to elongate the bladder 32' to the condition shown in the top of FIG. 2. This compresses the hydraulic fluid within the pump 12-2 and forces it out through the tube 36 to the hydraulic dynamic muscle 14-2 which expands to its maximum, and as it expands, it applies a tensive force to the cable 26 connected to its end. The cable, in turn, pulls the articulation section of the borescope to bend it upwards. The opposite hydraulic pump 12-1 and hydraulic muscle 14-1 for this plane of actuation are then in the exactly opposite condition, as shown, with the hydraulic muscle pump 12-1 being in its fully expanded and foreshortened condition and the hydraulic dynamic muscle 14-1 being in the stretched condition. The stretched condition is caused by the cable attached to the distal end of its bladder being pulled by the bending of the articulation section of the borescope.

In order to bend the borescope in the opposite direction, the control knob 44 will be operated to pull the bottom cable 26' to elongate the opposite bladder 32' in the hydraulic muscle pump 12-1. As it does, the tension on the other cable 26' of the pair will be eased, allowing the bladder 32' in pump 12-2 to relax to its more normal expanded configuration. As the process continues muscle 14-1 is fully expanded and pulls on cable 26 to move imager head 24 in the opposite or downward direction and hydraulic fluid is forced from bladder 32 in hydraulic muscle 14-2 to expand pump 12-2 and permit the tension applied to the cable 26 attached to muscle 14-1 to bend the articulated section 16 of the borescope in the downward direction as the bladder 32 in hydraulic dynamic muscle 14-1 is expanded and foreshortened.

In similar fashion, the other pair of hydraulic muscle pumps and hydraulic dynamic muscles not shown in FIG. 2 are actuated by the controller to move the distal end of the borescope insertion tube in a plane at ninety degrees to the plane of movement effectuated by the first pair.

It is thus seen that with this closed hydraulic system linking a hydraulic muscle pump and a hydraulic dynamic muscle, a completely self-contained actuation system is provided that has virtually eliminated all the deficiencies of the prior art cable systems, while maintaining the small diameter of the insertion tube and the simplicity and direct actuation control of the cable systems. Since the hydraulic muscle pumps function essentially in mirror image with the hydraulic dynamic muscles, good "feedback" is provided to the operator providing an appropriate and natural reaction to movement of the articulated end of the borescope. This force feedback to the operator improves the efficiency and accuracy of placement of the distal end of the borescope and simplifies the training required for the operator while still providing a superior, more accurate hydraulic actuation of the imager head 24.

Since the characteristics of the hydraulic pump are analogous to those of the hydraulic dynamic muscle, at the start of a full cycle, the braid angle of the muscle pump braid surrounding the bladder is at its greatest and therefore, the required cable force for a given output pressure is lowest and the motion of the pull is greatest. At the other end of the cycle, the braid angle is at its smallest and the required cable force for the same output pressure is highest, and the motion of the pull is smallest.

As indicated above, each unit of hydraulic muscle pump, connecting conduit, and hydraulic dynamic muscle is hermetically sealed at all junction points with the bladders, sleeves, conduit and actuating cables to form one self-contained actuating element. This is an important advantage of this invention, particularly for endoscope applications, since it greatly reduces the risks of leakage and contamination. Also, the present invention has eliminated all "working" fluid seals in the system such as piston rings, packing glands, etc. Furthermore, the "friction" losses due to the bladders is a small percentage of that encountered in usual cylinder/piston hydraulic or pneumatic systems which permits more sensitivity of control and/or greatly extended distance of control without loss of precision and accuracy. In one embodiment of this invention, accurate manipulation has been obtained at over fifty feet of coiled insertion tube between the control and the viewing head.

Further, it should be understood that while the invention is shown with the hydraulic pump muscle being a mirror image of the hydraulic dynamic muscle and disposed within the insertion tube, some embodiments of the present invention may have the hydraulic pump muscle located outside of the insertion tube with a much larger diameter and shorter length, for the same actuation capacity, than that shown in FIGS. 1 and 2.

In the preferred embodiment of this invention I have shown this closed hydraulic system as being used to actuate the articulation section of a borescope. It is believed apparent that this closed hydraulic system could be used for many other types of articulation requirements where a quantity of hydraulic fluid must be moved from one place to another through a connecting tube in order to actuate a device. Numerous robotic applications of the closed actuation system of this device can be readily visualized by those skilled in the art.

While the invention has been described in detail with reference to a preferred embodiment, it should be understood that the invention is not limited to that precise embodiment, that many modifications and variations thereof would present themselves to those skilled in the art without departing from the scope and spirit of this invention as defined in the appended claims.

What is claimed is:

1. A borescope or endoscope having a flexible elongated insertion tube, an articulation section at a distal end of said insertion tube, and at least a first pair of steering cables for bending the articulation section in one place comprising:
    at least one pair of liquid dynamic muscle means, each associated with their respective one of said steering cables in the distal end of said insertion tube;
    at least one corresponding pair of liquid pump means disposed adjacent the proximal end of said insertion tube;
    liquid conduit means extending from the proximal end of said liquid dynamic muscle means to the distal end of the corresponding liquid pump means for transferring liquid from one to the other; and
    control means operatively connected to said pump means for selectively forcing liquid therefrom and into the corresponding liquid dynamic muscle means.

2. A device as described in claim 1 further including two pair of steering cables for bending the articulation section in two directions; two pair of liquid dynamic muscles operatively connected to said steering cables disposed so as to bend said insertion tube in two different planes perpendicular to each other; and two pair of liquid pumps disposed adjacent the proximal end of said insertion tube.

3. A borescope or endoscope as defined in claim 1 wherein said hydraulic dynamic muscles and their corresponding liquid pumps and liquid conduits comprise a hermetically sealed unit and have enough liquid therein for one of said muscles to be in an elongated condition, and the corresponding other muscle to be in an expanded condition.

4. A device as described in claim 1 wherein each of said liquid dynamic muscles and liquid pumps comprises:
    an elongated elastomeric bladder;
    a tubular braid member with proximal and distal ends, disposed over each bladder, and formed of a plurality of flexible substantially inextensible filaments, the tubular braid permitting said bladder therewithin to expand laterally when said liquid is forced into it, but restraining the bladder such that as said tubular braid increases in diameter, it contracts axially;

a semi-rigid tubular sheath positioned about each said braid and bladder portions of said pairs of liquid dynamic muscles and liquid pumps;

anchor means for anchoring a first end of each of said tubular braid members to a first end of the sheath on each of said pairs of liquid dynamic muscles and liquid pumps;

a termination closing the other end of each of said tubular braid members;

tendon means connected to said termination for carrying a tensive force from said braid members to one of said steering cables or control means.

5. The borescope or endoscope of claim 4 further defined by said bladders and connecting conduit being a hermetically sealed unit and having enough liquid therein for one of said bladders to be in an elongated condition and the other of said bladders to be an expanded condition.

6. A borescope or endoscope that comprises a flexible elongated insertion tube, having an articulation section at a distal end of said insertion tube with two pairs of steering cables for bending the articulation section, two pair of hydraulic dynamic muscles each associated with a respective one of said steering cables, and two pair of hydraulic muscle pumps each associated with a respective one of said dynamic muscles, each of said muscles and pumps including:

an elongated elastomeric bladder;

a hydraulic fluid conduit extending from the proximal end of each associated muscle bladder to the distal end of each associated pump bladder in said pair for transmission of hydraulic fluid pressure from the pump to the muscle bladder;

a tubular braid, with proximal and distal ends, disposed over each bladder associated with the hydraulic dynamic muscle and the hydraulic muscle pump formed of a plurality of flexible substantially inextensible filaments, the tubular braid permitting said bladder therewithin to expand laterally when said hydraulic fluid pressure is applied to it, but restraining the bladder such that as said tubular braid increases in diameter, it contracts axially;

a semi-rigid tubular sheath positioned about each said braid and bladder portions of said pairs of hydraulic dynamic muscles and hydraulic muscle pumps;

anchor means for anchoring the proximal end of said braid tot he proximal end of the sheath on each hydraulic dynamic muscle;

anchor means for anchoring the distal end of said braid to a distal end of said sheath for each of said hydraulic muscle pumps;

a termination closing the distal end of said tubular braid on each of said hydraulic dynamic muscles;

means connecting said steering cables to said muscle termination for carrying a tensive force from said hydraulic dynamic muscle braid to pull said articulation section when hydraulic fluid pressure causes said bladder and braid to expand;

a substantially incompressible cable sheath over said steering cables extending between said articulation section and a distal end of said muscle tubular sheath for carrying compressive reaction forces to said hydraulic dynamic muscle from said articulation section;

a termination closing the proximal end of said tubular braid on each of said hydraulic muscle pumps;

control means for selectively applying a tensive force to said braid disposed about said pump bladders;

cable means connected to said pump termination for carrying a tensive force from said braid to said control means; and compression bearing means connecting said hydraulic muscle pump semi-rigid tubular sheath to said control means to that actuation of said control means actuates one of said hydraulic muscle pumps causing hydraulic fluid pressure to be applied to the associated hydraulic dynamic muscle in such fashion as to bend said articulation section a desired degree.

7. A borescope as described in claim 6 wherein said hydraulic dynamic muscles are positioned within the insertion tube near the distal end thereof adjacent said steering cables and said hydraulic muscle pumps are situated within the insertion tube near the proximal end thereof to minimize play in the steering cables while allowing use of greatly elongated insertion tubes.

* * * * *

UNITED STATES PATENT AND TRADEMARK OFFICE
CERTIFICATE OF CORRECTION

PATENT NO.   : 4,962,751
DATED        : October 16, 1990
INVENTOR(S)  : ALLAN I. KRAUTER It is certified that error appears in the above—identified patent and that said Letters Patent is hereby corrected as shown below:

Col. 6, line 33, please change "place" to --plane--.

Col. 8, line 7, please change "tot he" to --to the--.

Signed and Sealed this

Thirty-first Day of March, 1992

Attest:

HARRY F. MANBECK, JR.

*Attesting Officer*          Commissioner of Patents and Trademarks